US00PP08927P

United States Patent [19]

Van der Salm

[11] Patent Number: Plant 8,927

[45] Date of Patent: Oct. 4, 1994

[54] LILIUM 'YELLOW GRACE'

[76] Inventor: Gerardus C. Van der Salm, 35210 NW. Toenjes Rd., Woodland, Wash. 98674

[21] Appl. No.: 186,700

[22] Filed: Jan. 25, 1994

[51] Int. Cl.[5] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing large upfacing flowers of excellent form and long persistence, both on the plant and as cut-flowers. The flowers of the new plant are particularly characterized by their exceptional substance, deep yellow coloring, their small brushmarks and inconspicuous spotting, their starry form with tepals only slightly overlapping, their narrow green nectary furrows with yellow pubescent margins, and their semi-umbellate inflorescence. 'Yellow Grace' has attractively ascending foliage and forces well even under extremely warm conditions. This combination is completely new in the Asiatic hybrid divisions of lilies suited to forcing and to mass commercial cultivation. The variety is highly resistant to Fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in Julianadorp, the Netherlands, in 1986. The breeding efforts had as their objective the production of large-flowered upfacing Asiatic hybrids in shades of yellow and orange, with attractive but small brush-marks, suited to forcing into flower out of season in a variety of climates, heretofore unknown in the lily breeding art.

I achieved the desired objective by intercrossing unnamed upright yellow and orange Asiatic seedlings which showed a variety of brush-mark patterns and which were also suited to forcing for year-round use as cut-flowers. The unnamed Asiatic seedlings which were the parents of 'Yellow Grace' were produced by me, from a series of crosses among seedlings which were selected in my fields from large seedling populations of my own crosses. The original crosses came from material unique to my own breeding lines and not available in the trade. The field-selected seedlings were genetically very diverse, and 100 seedlings were selected for their outstanding vigor, stem length, non-fading yellow or orange flower color, attractive brush-marks, upfacing flower orientation, and well-spaced inflorescence. These were forced into flower under glass, and the 25 seedlings which showed the best forcing performance were then randomly intercrossed to produce a large quantity of seed. This seed was grown to flowering size, producing a large population of seedlings, from which the best 100 were again selected for vigor, stem length, non-fading yellow or orange flower color, attractive brush-marks, upfacing flower orientation, and well-spaced inflorescence. These were subsequently tested for their forcing performance, and 'Yellow Grace' was selected as one of the yellow-flowering, lightly brush-marked seedlings best suited to forcing as a cut-flower.

The flowers of my new lily are characterized by an upfacing orientation, large size, exceptional substance, deep yellow coloration with attractively small brush-marks and inconspicuous spotting, narrow green nectary furrows with yellow pubescent margins, and a starry flower form with tepals only slightly overlapping, a combination unique among Asiatic hybrid lilies. The foliage is ascending, an advantage in packing the stems when 'Yellow Grace' is forced as a commercial cut-flower, and the inflorescence is semi-umbellate. The variety possesses unusually tall, strong, stout stems. In addition, the clone possesses to a high degree desirable characteristics of hybrid vigor. The clone is a good grower and propagator, as observed in Julianadorp, the Netherlands.

My new variety of lily plant has been asexually reproduced by me and under my direction at Julianadorp, the Netherlands. Successive generations produced by natural propagation from bulblets, by bulb scale propagation, and by tissue culturing from bulb scale explants have demonstrated that the novel and distinctive characteristics of my new variety are fixed and hold true under asexual propatation from generation to generation.

DESCRIPTION OF THE DRAWING

My new variety of lily plant is illustrated in the accompanying photographic drawings, which show the open bloom in full color and illustrate the starry flower form, the tepal arrangement, the semi-umbellate inflorescence, the ascending foliage, and in particular the novel and distinctive upfacing deep yellow flowers with attractive small brushmarks, inconspicuous spotting, narrow green nectary furrows with yellow pubescent margins, and slightly overlapping tepals.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Seedling.

Seed parent: Selected unnamed Asiatic hybrid seedling.

Pollen parent: Selected unnamed Asiatic hybrid seedling.

Commercial classification: Hybrid Lilium clone.

Horticultural classification: Division IA, Upright Asiatic hybrid lily, according to the Horticultural Classification of Lilies, Royal Horticultural Society of London.

Form: Single stem, erect and stately.

Height: 80 to 125 cm from bulbs 14 to 18 cm in circumference, provided their light levels are adequate; low light levels may cause "stretching."

Growth: Vigorous and upright, with leaves ascending, forming an angle of 20 to 50 degrees from the vertical axis of the stem.

Internode length: Typically 1–2 cm at mid-stem.

Foliage quantity: Abundant.

Size of leaf: 15 to 25 mm wide×10 to 14 cm long.

Shape of leaf: Lanceolate (pointed).

Texture: Leathery and glossy.

Color: Medium green, lighter on lower side.

Bulb:

*Size.*—Any size, ranging to 25 cm circumference commercially.

*Color.*—White, with flushes of pink or yellow after exposure to light.

The Bud

Form: Obtuse, ovoid, and long.

Size: 7 to 9 cm long and 8 to 12 cm in circumference just prior to opening.

Opening: Bud opens slowly, in response to morning light; this takes about one hour.

Color: Soft yellow (R.H.S. CC yellow 8 B/C) with apple green mid-ribs and apex. The green color fades and the yellow color deepens to the intensity of the flower color immediately prior to opening.

Peduncle: Averages 10 to 12 cm, but it may elongate if light levels are too low or if bulbs have been improperly stored prior to forcing. Color is medium green.

The Flower

Blooming habit: Annually in midseason; flowers once and profusely.

Size: Flowers are large-sized, averaging 15 to 17 cm in diameter, reflexing at the tips on the second day to 14 to 16 cm in diameter. The outer tepals are 22 to 30 mm wide, and inner tepals are 25 to 35 mm wide. Tepals typically are only slightly overlapping.

Borne: In a single racemic inflorescence producing 4 to 8 flowers from a bulb 14 to 16 cm in circumference.

Shape: Flower opens broadly and tepal tip recurve to form a flat face by the second day after opening.

Tepalage: Typical of genus Lilium, with 6 imbricated tepals.

Tepal:

*Color.*—R.H.S. CC Yellow 9 A/B to 13 A/B. Flower deepens to the more intense and lightly golden RHS 13 A/B as the flower ages and under conditions of bright light. Newly-opened flowers and those grown under low light conditions will show the slightly less gold RHS 9 A/B.

Spotting.—The basal third to half of each tepal carries 10–30 small and inconspicuous deep magenta papillae, parallel to the apex of the nectaries or just above it. Outer tepals typically show a small brushmark, 5 to 10 mm long and 10 to 12 mm wide, centered along the midrib, extending from the nectary furrow. Inner tepals may show a longer but typically narrower and lighter brushmark, usually 5 cm wide and 10–20 cm long, extending from the nectary furrows along the midrib. Light levels just prior to the opening of the bud strongly affect the extent and color intensity of the brushmarks: under very low light levels, no brushmarks will be apparent; with moderate light levels, the outer tepals will be affected but not the inner tepals; and with bright light levels, all tepals will show brushmarks. The brighter the light levels, the more intense the coloring of the brushmarks. The brushmarks are typically R.H.S. CC 182–183 A/B, but under bright light, they may approach R.H.S. CC 46 A to 53 A.

*Longevity.*—Tepals stay on stems about three weeks.

Pedicel:

*Length.*—Average 10 to 15 cm long.

*Color.*—Medium green.

*Form.*—Sturdy and ascending.

Color changes: Flowers become slightly deeper and more golden yellow as the flowers age, under bright light conditions. Low light levels may cause the flowers to become slightly lighter and less golden yellow.

Appearance: Flower is shiny.

Nectaries: Present on both inner and outer tepals; light green, narrow, and inconspicuous nectary furrow with soft yellow pubescent margins.

Disease resistance: The flower and plant are resistant to disease; in particular they are resistant to Fusarium bulb rot and Botrytis blight.

Fragrance: None.

Lasting quality: The flower is long lasting, both on the plant and as a cut-flower.

The Reproductive Organs

Stamens: Arrangement typical of genus Lilium. Six stamens with soft yellow (R.H.S. CC yellow 8 C to 13 C) to white filaments 5 to 7 cm long.

Pollen and anthers (dehisced): R.H.S. CC greyed orange 171 A to 174 A.

Pistil: One in number, 5 to 7 cm long.

Stigma: Soft green occasionally overlaid with R.H.S. CC greyed red 182 D, medium in size.

Characteristics of ovary: Characteristic of genua Lilium.

The Fruit

Fertility: The fruit bears fertile seed.

Shape: Ovoid.

Color at maturity: Soft brown, sometimes overlaid with soft plum.

My new variety of Asiatic hybrid lily most nearly resembles 'Dayspring' (U.S. Plant Pat. No. 4,181), but its flowers differ from those of 'Dayspring' in their deeper yellow coloration, much less conspicuous spotting which is confined to smaller area of the flower, small brushmarks, unfrilled tepal margins, and starrier flower form with only slightly overlapping tepals. It somewhat resembles 'Flirt' (unpatented). The flowers of 'Flirt,' however, differ from those of 'Yellow Grace' in their more conspicuous and darker brushmarks, much lighter yellow coloration, much more broadly overlapping tepals, lightly frilled tepal margins, shorter pedicels, and clearly racemose inflorescence. 'Flirt' is also much shorter than 'Yellow Grace.'

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower producer from pre-cooled bulbs forced under glass out of season; and in particular by its unique upfacing flowers showing deep yellow coloration, inconspicuous spotting and small brushmarks, narrow green nectaries with soft yellow pubescent margins, starry flower form with only slightly overlapping tepals, and semi-umbellate inflorescence, a combination unique among Asiatic hybrid lilies suited to forcing and to mass commercial cultivation.

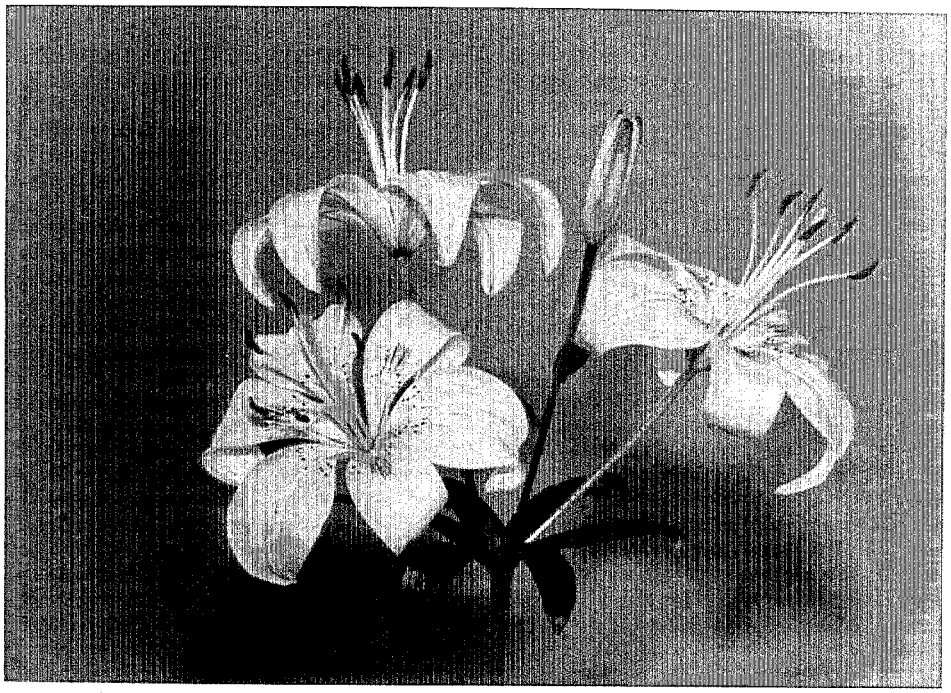
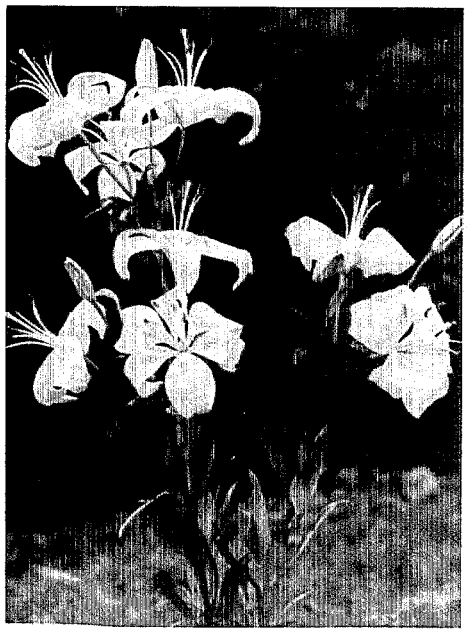

* * * * *